Sept. 24, 1957 E. S. BOERNER Plant Pat. 1,643
ROSE PLANT
Filed Jan. 7, 1957
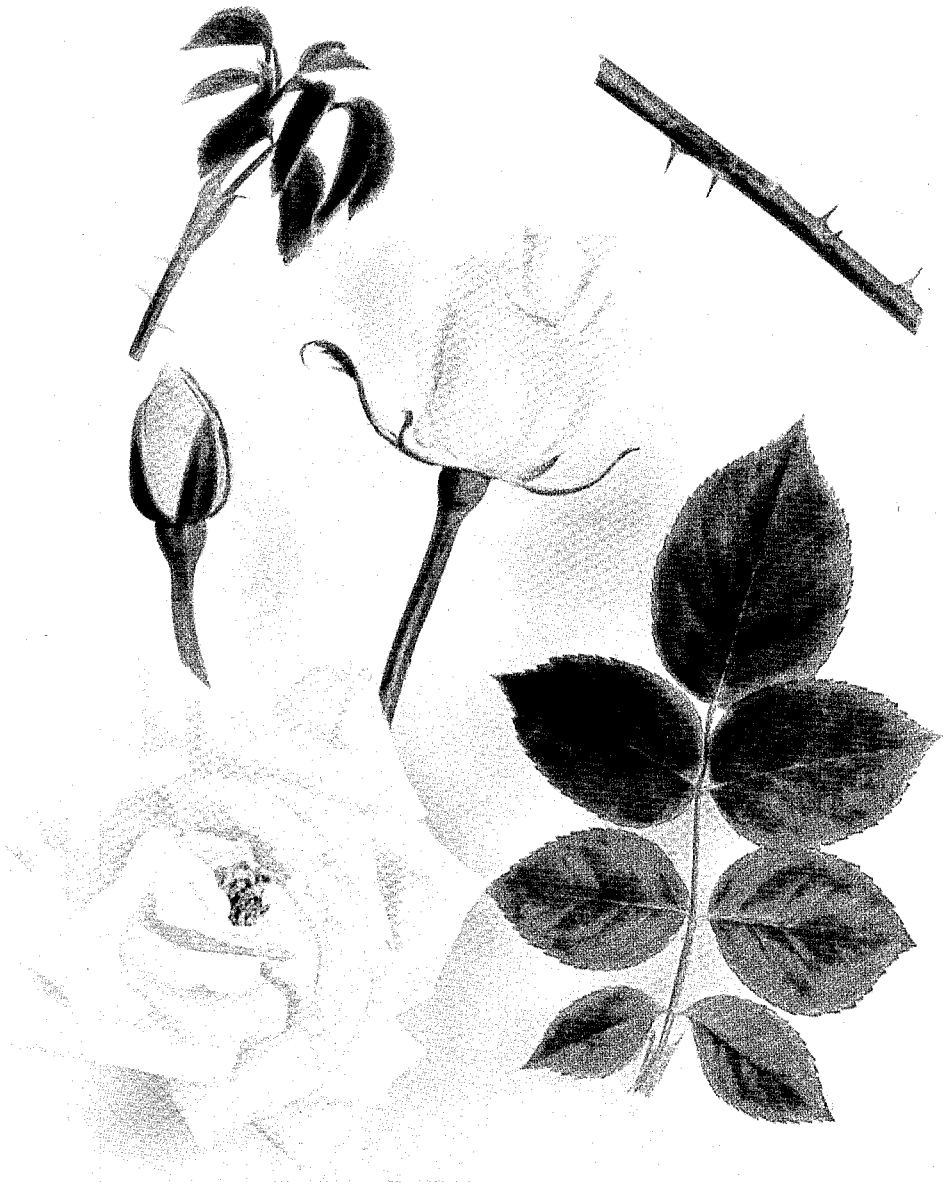
Inventor
E. S. Boerner
By: Robb & Robb
Attorneys.

United States Patent Office

Plant Pat. 1,643

Patented Sept. 24, 1957

1,643

ROSE PLANT

Eugene S. Boerner, Newark, N. Y., assignor to Jackson & Perkins Company, Newark, N. Y., a corporation of New York Application January 7, 1957, Serial No. 632,954

1 Claim. (Cl. 47—61)

The present invention relates to a new and distinct variety of rose plant of the hybrid tea class, which was originated by me by crossing two unnamed and unpatented yellow hybrid tea seedlings.

The primary objective of this breeding was to produce a new rose variety of the hybrid tea class which is very free and prolific in its flower production and suitable for cut flower forcing, with the flowers maintaining a golden yellow color in all stages of bloom. This objective was fully achieved, along with other improvements, as evidenced by the following characteristics which are outstanding in the new variety and distinguish it from its parents, as well as from all other varieties of its class of which I am aware:

(1) The very free and prolific flower producing habit;

(2) The Apricot Yellow, lightly overcast with Empire Yellow, general color tonality of the flowers;

(3) The consistent coloration of the flowers in all seasons and in all stages from the bud stage through the final open flowers; and (4) The extremely rich and glossy foliage which provides an effective background for the buds and flowers.

Asexual reproduction of the new variety by budding, as performed at Newark, New York, and also at Pleasanton, California, shows that the foregoing characteristics and distinctions come true to form and are established and transmitted through succeeding propagations.

The accompanying drawing shows typical specimens of the vegetative growth and flowers of the new variety in different stages of development and as depicted in color as nearly true as it is reasonably possible to make the same in a color illustration of this character.

The following is a detailed description of the new variety, with color terminology in accordance with Ridgway's Color Standards and Nomenclature:

Parentage: Seedling.

*Seed parent.*—An unnamed yellow hybrid tea seedling.

*Pollen parent.*—An unnamed yellow hybrid tea seedling.

Classification:

*Botanic.*—Hybrid tea.

*Commercial.*—Hybrid tea.

*Flower*

(Observations made from specimens grown in a greenhouse at Newark, New York, in the early morning and in the early part of September.)

Blooming habit: Recurrent—continuous.

Bud:

*Size.*—Medium.

*Form.*—Ovoid; is not affected by wet or hot weather.

*Color.*—

When sepals first divide—Pale Greenish Yellow, Plate 5. When petals begin to unfurl—Lemon Chrome, Plate 4, lightly overcast with Apricot Yellow, Plate 4. When half-blown: inside of petals—Apricot Yellow, Plate 4, lightly overcast with Lemon Chrome, Plate 4; reverse of petals—Light Cadmium, Plate 4, lightly overcast with Lemon Chrome, Plate 4.

*Sepals.*—Slightly branched; curl back when petals begin to unfurl. Color: inside—Pale Fluorite Green, Plate 32; outside—Bice Green, Plate 27.

*Calyx.*—Color—Bice Green, Plate 27. Shape—pear. Size — small. Aspect — smooth. Odor when rubbed—none.

*Peduncle.*—Length — medium. Aspect — prickly. Strength—erect; slender. Color—Cedar Green, Plate 6.

*Opening.*—Opens up well; is not affected by adverse weather conditions.

Bloom:

*Size.*—Large. Average size when fully expanded—5 inches.

*Borne.*—Both singly and several together.

*Stems.*—Medium length; strong.

*Form (when first open).*—Cupped. Permanence—retains its form to the end, but outer petals curl back.

*Petalage.*—Double (full but open center). Number of petals under normal conditions—from 30 to 35.

*Color.*—Center of flower—Apricot Yellow, Plate 4. Outer petals—Pinard Yellow, Plate 4. Base of petals (aiglet)—Lemon Chrome, Plate 4. Inside of petals—Apricot Yellow, Plate 4, lightly overcast with Empire Yellow, Plate 4. Reverse of petals—Maize Yellow, Plate 4. General tonality from a distance—Apricot Yellow, Plate 4, lightly overcast with Empire Yellow, Plate 4.

*Discoloration.*—General tonality at end of first day—Apricot Yellow, Plate 4. Second day—Apricot Yellow, Plate 4, lightly overcast with Empire Yellow, Plate 4. Third day—Apricot Yellow, Plate 4, overcast with Empire Yellow, Plate 4.

Petals:

*Texture.*—Leathery; is not affected by wet or hot weather.

*Appearance.*—Inside—satiny. Outside—shiny.

*Form.*—Oval.

*Arrangement.* — Imbricated (regularly arranged shingle-like).

*Petaloids in center.*—Few; large.

*Persistence.*—Drop off cleanly.

*Fragrance.*—Strong. Nature—tea (average hybrid tea scent).

*Lasting quality.*—On the plant—very long. As cut flower—very long.

*Genital organs*

Stamens, anthers: Medium size; many; regularly arranged around styles. Color—Orange Rufous, Plate 2.

Stamens, filaments (threads): Long. Color—Light Salmon-Orange, Plate 2.

Pollen: Color—Pale Yellow Orange, Plate 3.

Styles: Columnar; uneven length; medium length; thin.

Stigmas: Color—Bittersweet Orange, Plate 2.

Ovaries: Some protruding from calyx.

Hips: None.

Seeds: None.

*Plant*

Form: Bush.

Growth: Vigorous; upright.

Foliage: Compound of 5 to 7 leaflets.

*Size.*—Medium.

*Quantity.*—Normal.

*Color.*—New foliage: upper side—Parrot Green, Plate 6, lightly overcast with Vandyke Red, Plate 1; under side—Vandyke Red, Plate 1, lightly overcast with Yellowish Oil Green, Plate 5. Old foliage: upper side—Cress Green, Plate 31; under side—Light Elm Green, Plate 17.

*Shape.*—Oval pointed.

*Texture.*—Upper side—glossy. Under side—smooth.

*Ribs and veins.*—Ordinary.

*Edge.*—Serrated (saw toothed).

*Serration.*—Both double and single; small.

*Leaf stem.*—Color—Lumiere Green, Plate 17. Under side—smooth.

*Stipules.*—Long; smooth.

Wood:

*New wood.*—Color—Chromium Green, Plate 32. Bark—smooth.

*Old wood.*—Color—Varley's Green, Plate 18. Bark—smooth.

Thorns:

*Thorns.*—Quantity: on main stalks from base—few; on laterals from stalk—few. Form—narrow base; medium length; hooked downward. Color (when young)—Eugenia Red, Plate 13. Position—irregular.

*Prickles.*—Quantity: on main stalks—none; on laterals—none.

*Short needles.*—Quantity: on main stalks—none; on laterals—none.

I claim:

A new and distinct variety of rose plant of the hybrid tea class, substantially as herein shown and described, characterized particularly as to novelty by its very free-producing flower habit, the Apricot Yellow, lightly overcast with Empire Yellow, general color tonality of its flowers, the consistent flower coloration in all seasons and in all stages from the bud to the final open flower, and the extremely rich and glossy foliage which forms an effective background for the buds and flowers.

No references cited.